United States Patent
Nasser et al.

(10) Patent No.: US 10,940,287 B2
(45) Date of Patent: Mar. 9, 2021

(54) URINARY CATHETER FOR FACILITATING CONTROL OF BLADDER CONTENT VOLUME AND METHODS FOR USE THEREOF

(71) Applicant: Memorial Sloan-Kettering Cancer Center, New York, NY (US)

(72) Inventors: Nicola J. Nasser, Bronx, NY (US); Michael J. Zelefsky, New York, NY (US)

(73) Assignee: MEMORIAL SLOAN-KETTERING CANCER CENTER, New York, NY (US)

( * ) Notice: Subject to any disclaimer, the term of this patent is extended or adjusted under 35 U.S.C. 154(b) by 377 days.

(21) Appl. No.: 16/490,403

(22) PCT Filed: Dec. 18, 2015

(86) PCT No.: PCT/US2015/066845
§ 371 (c)(1),
(2) Date: Aug. 30, 2019

(87) PCT Pub. No.: WO2016/100901
PCT Pub. Date: Jun. 23, 2016

(65) Prior Publication Data
US 2020/0368492 A1   Nov. 26, 2020

Related U.S. Application Data

(60) Provisional application No. 62/094,123, filed on Dec. 19, 2014.

(51) Int. Cl.
*A61M 25/10* (2013.01)
*A61M 25/00* (2006.01)

(52) U.S. Cl.
CPC .... *A61M 25/0017* (2013.01); *A61M 25/0074* (2013.01); *A61M 25/1011* (2013.01);
(Continued)

(58) Field of Classification Search
CPC .......... A61M 25/1011; A61M 25/0017; A61M 25/0074; A61M 2025/1015; A61M 2210/1085; A61M 2025/0079
See application file for complete search history.

(56) References Cited

U.S. PATENT DOCUMENTS

| 5,306,226 A | 4/1994 | Salama |
| 5,417,657 A | 5/1995 | Hauer |

(Continued)

FOREIGN PATENT DOCUMENTS

| AU | 2004206975 B2 | 9/2004 |
| WO | 2009046176 A1 | 4/2009 |

OTHER PUBLICATIONS

International Search Report and Written Opinion dated May 17, 2016 for PCT/US2015/066845.

*Primary Examiner* — Kai H Weng
(74) *Attorney, Agent, or Firm* — Hunton Andrews Kurth LLP

(57) ABSTRACT

An exemplary catheter can be provided which can include, for example, a first inflation arrangement configured, in operation, to substantially seal and/or anchor the catheter inside the bladder when inflated, a second inflation arrangement configured, in operation, to substantially float in urine when inflated, wherein the second arrangement can be located at a predetermined distance from the first inflation arrangement, and an aperture provided between the first inflation arrangement and the second inflation arrangement, where the first and second arrangements can cause the aperture to be (i) open when the second inflation arrangement can be located at a first position relative to the first (Continued)

Full bladder inflation arrangement, and (ii) closed when the second inflation arrangement can be located at a second position relative to the first inflation arrangement, and where the second position can be different than the first position.

15 Claims, 15 Drawing Sheets

(52) U.S. Cl.
CPC ............... *A61M 2025/0079* (2013.01); *A61M 2025/1015* (2013.01); *A61M 2210/1085* (2013.01)

(56) References Cited

U.S. PATENT DOCUMENTS

| | | | |
|---|---|---|---|
| 5,429,620 | A | 7/1995 | Davis |
| 7,780,640 | B1 | 8/2010 | Amador |
| 2002/0077625 | A1 | 6/2002 | Lev |
| 2004/0102826 | A1 | 5/2004 | Lasheras et al. |
| 2005/0054994 | A1 | 3/2005 | Cioanta et al. |
| 2006/0212022 | A1* | 9/2006 | Gellman ............ A61M 25/1011 604/509 |
| 2012/0259216 | A1* | 10/2012 | Gerrans ......... A61B 17/320725 600/435 |

* cited by examiner

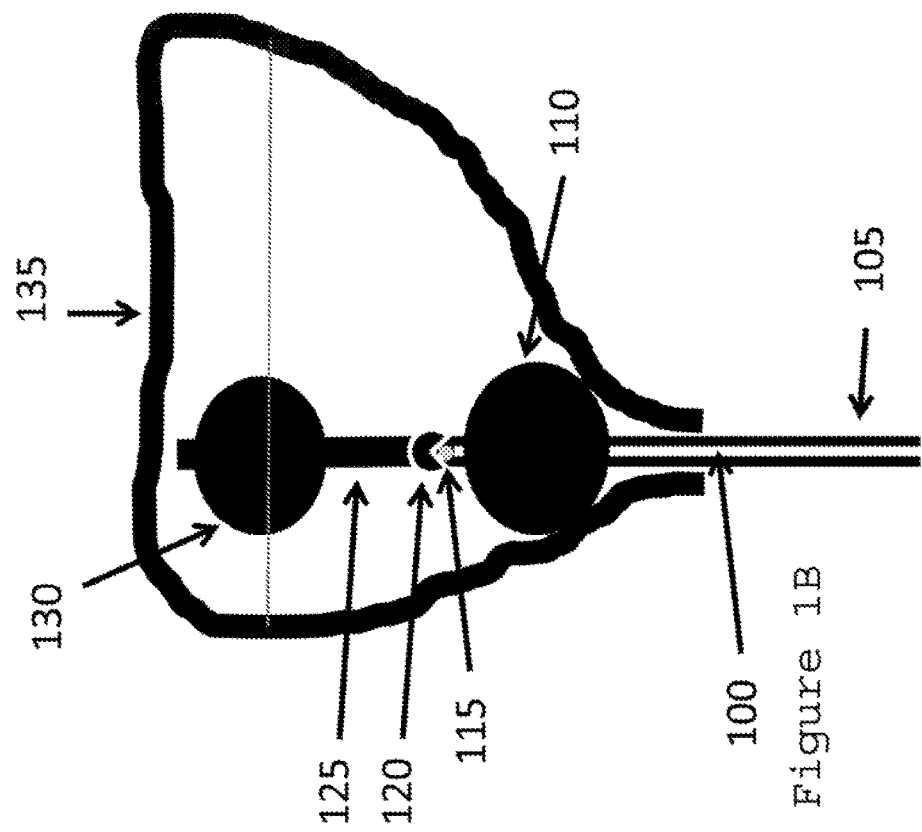
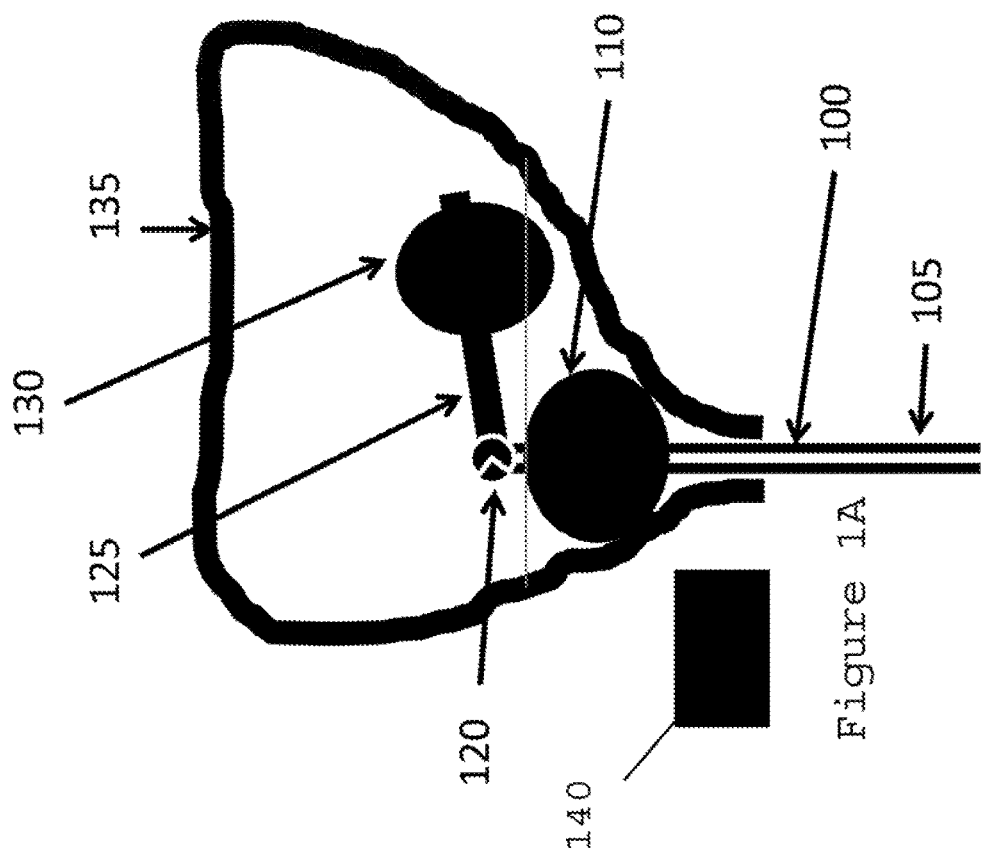

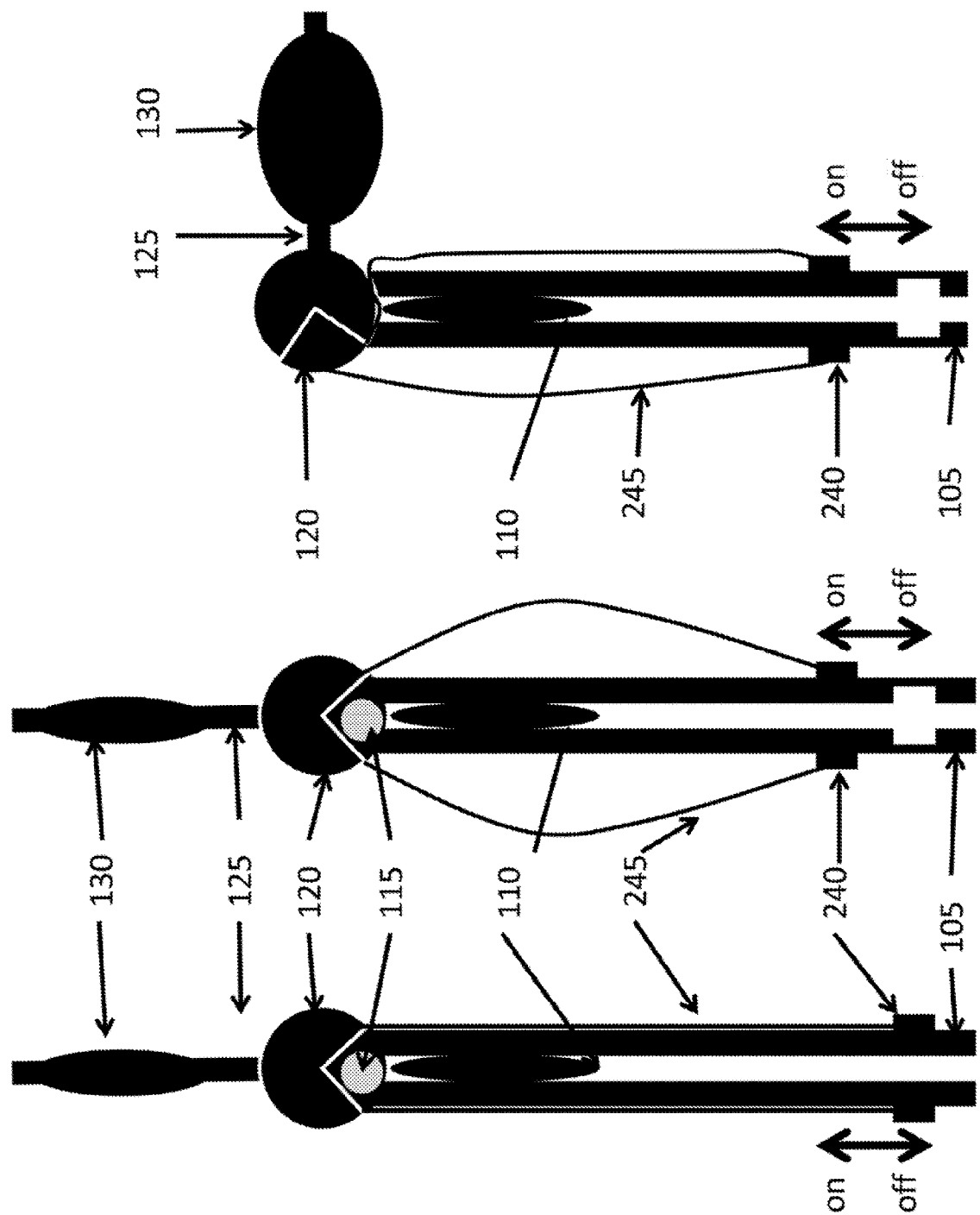

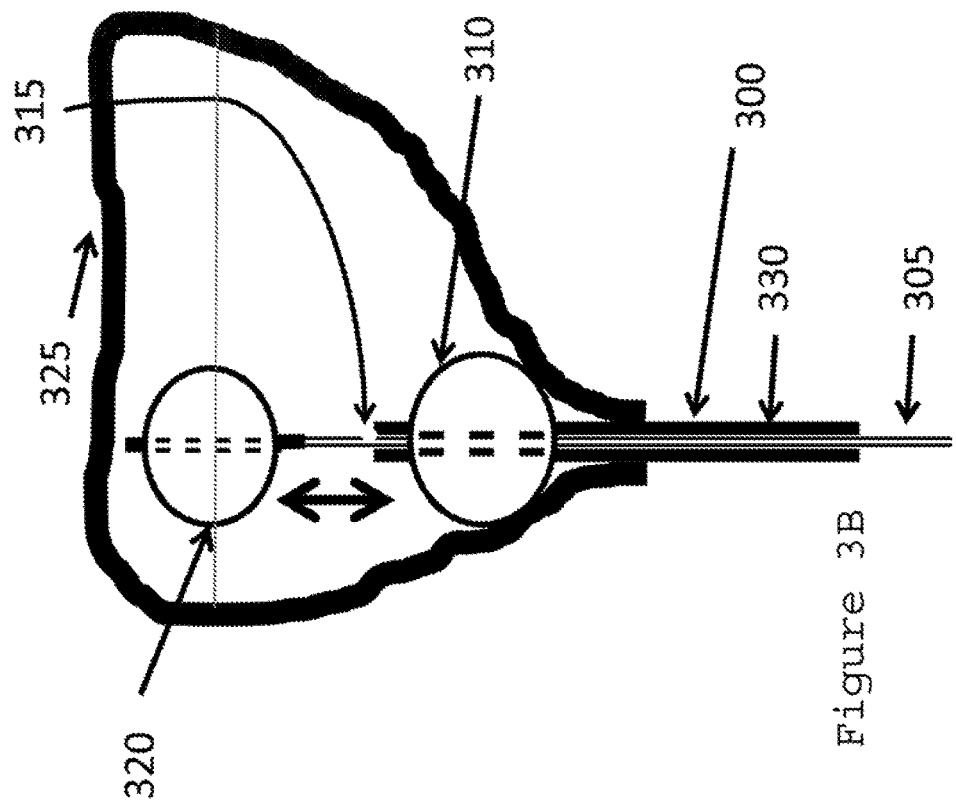
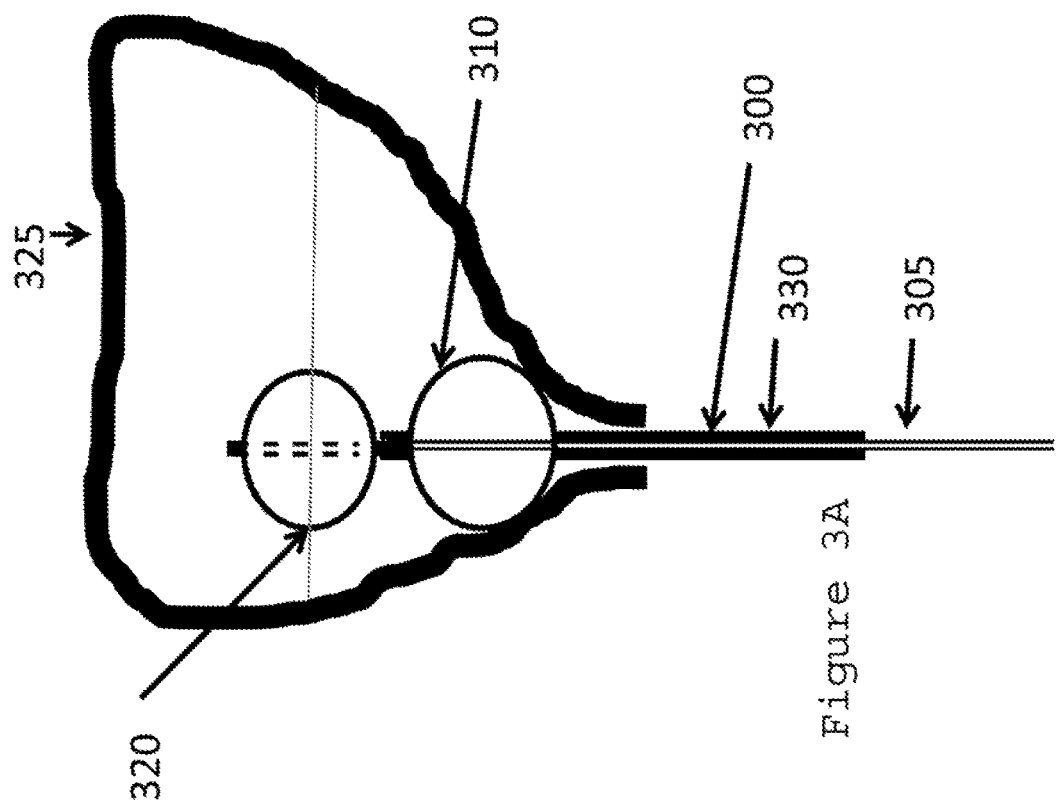

Full bladder

Empty bladder

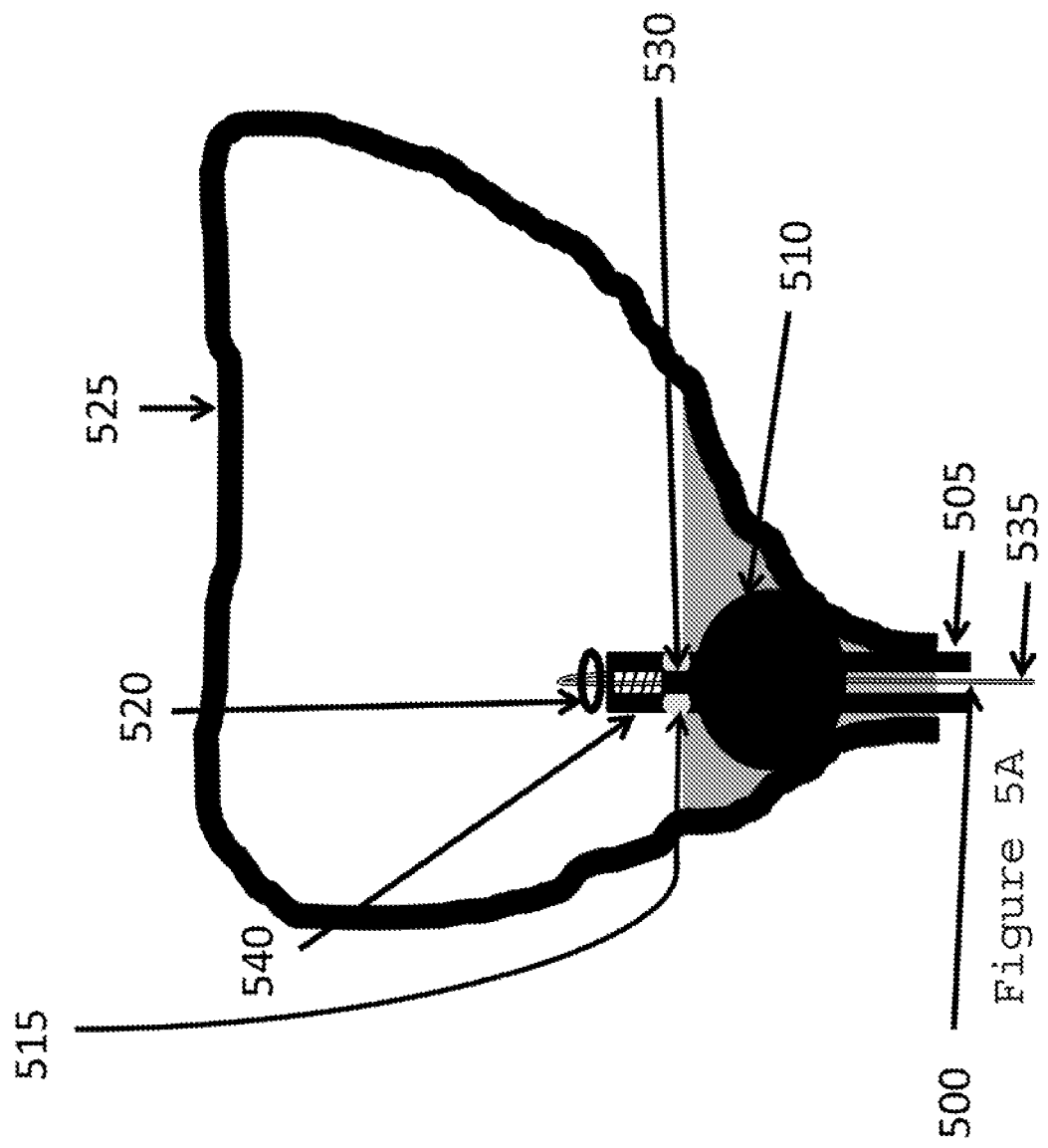

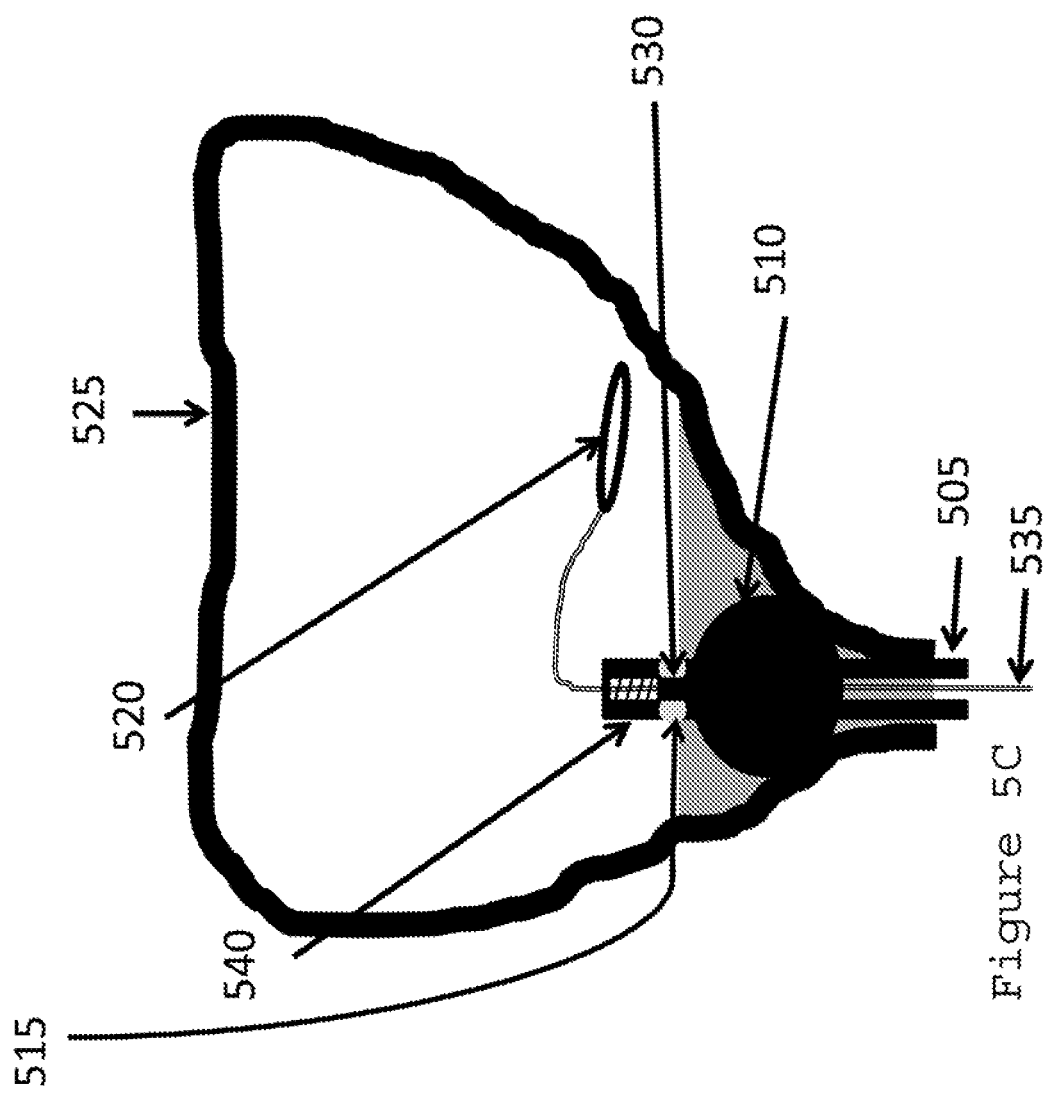

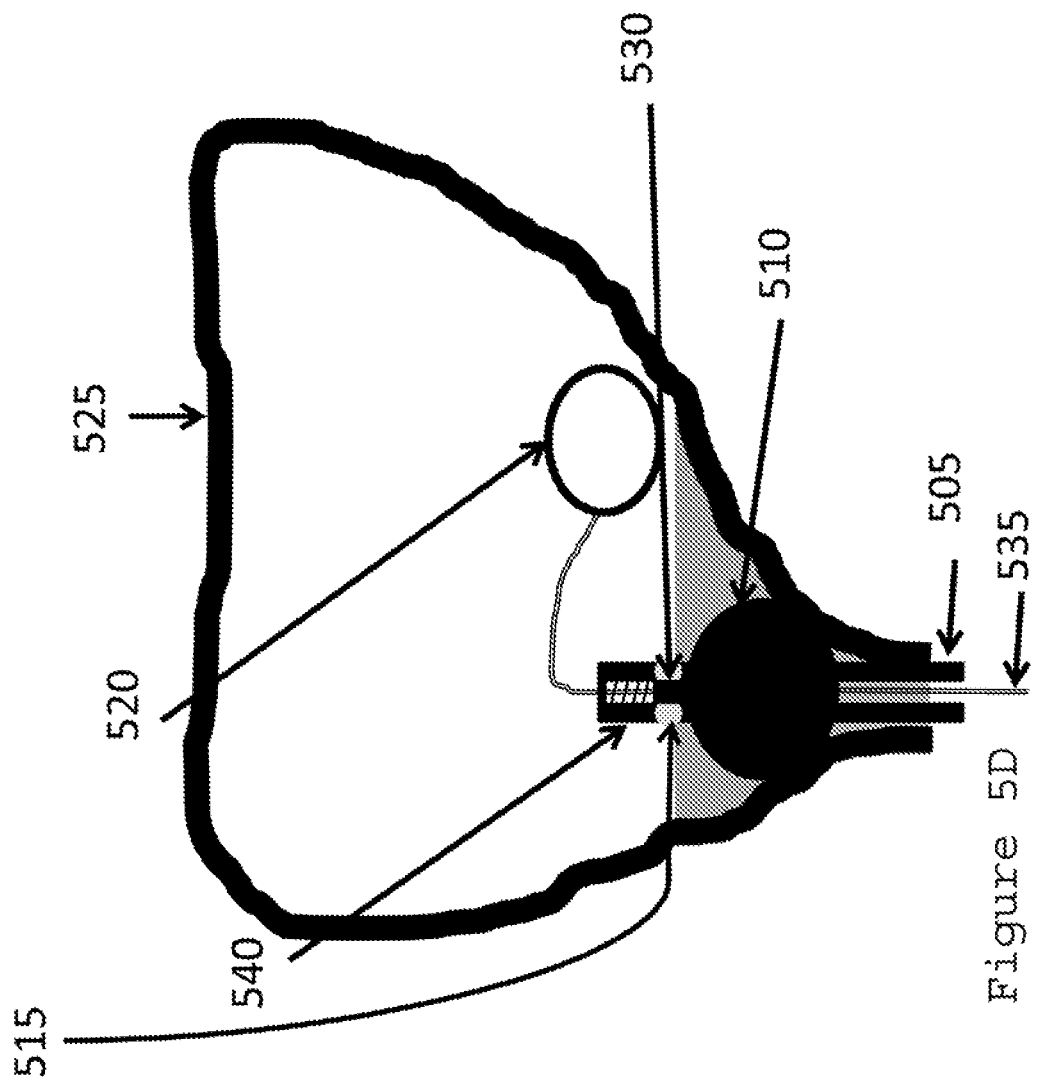

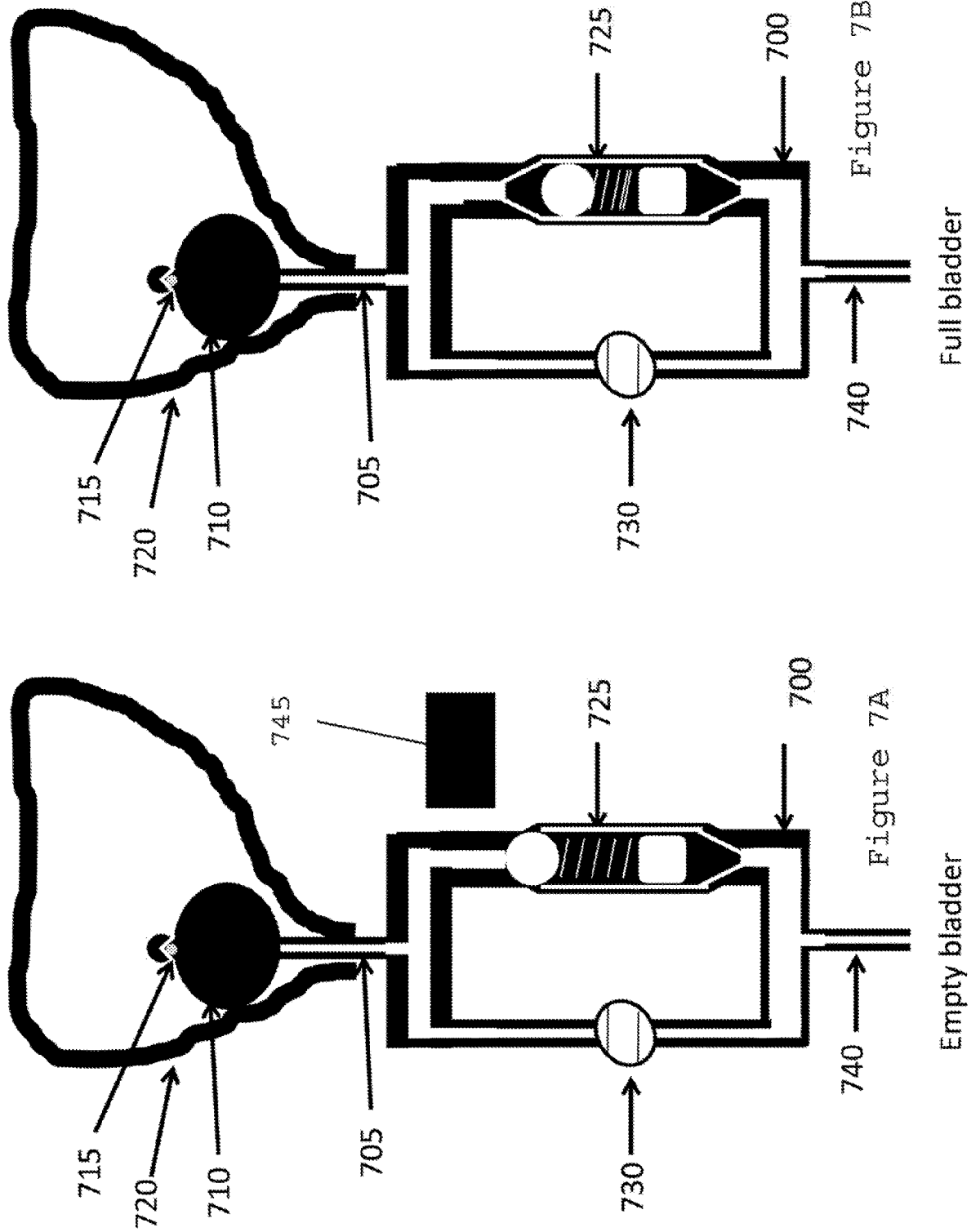

URINARY CATHETER FOR FACILITATING CONTROL OF BLADDER CONTENT VOLUME AND METHODS FOR USE THEREOF

CROSS REFERENCE TO RELATED APPLICATION(S)

The present application relates to and claims priority from International Patent Application No. PCT/US2015/066845 filed Dec. 18, 2015 which published as International Publication No. WO 2016/100901 on Jun. 23, 2016 and from U.S. Patent Provisional Application No. 62/094,123, filed Dec. 19, 2014, the entire disclosures of which are incorporated herein by reference.

FIELD OF THE DISCLOSURE

The present disclosure relates generally to a catheter, and more specifically, to exemplary embodiments of a urinary catheter configured to control bladder content volume, and methods for use thereof.

BACKGROUND INFORMATION

External beam radiation therapy to the pelvis is the standard of care for a variety of malignancies such as rectal, anal, uterine and prostate cancers. Radiation therapy applied to the pelvis attempts to deliver a cytotoxic radiation dose to the tumor and the areas at risk for tumor metastasis such as lymph nodes, while also limiting the dose to normal body structures so as not to damage the normal body structures. Different body organs have various tolerances to radiation. For example, the small bowel can be much more sensitive to radiation than the bladder. Radiation to the small bowel can result in side effects such as abdominal pain, vomiting, diarrhea, bowel obstruction, perforation and/or bleeding. Therefore, radiation therapy applied to pelvic malignancies is preferably delivered while the patient's bladder is full with urine in order to push the small bowel out of the radiation fields, and to decrease the volume of radiation received by the small bowel.

The computerized tomography ("CT") simulation for planning of radiation therapy, and the delivery of radiation treatment fractions, should preferably be performed while the bladder is full with approximately the same amount of fluid in each session. However, currently there is no precise way to control the volume of urine in the bladder, and patients are usually instructed to urinate, drink a certain amount of water within specified time before radiation and be hopeful that they will have approximately the same amount of urine in their bladder at each treatment session. An ultrasound evaluation of the urine volume in the bladder can be performed before the treatment to quantify the urine the volume in the bladder, and if the urine volume is not at a specific preset level, the patient is instructed to wait, and drink water, and have the measurement of the urine repeated until the specified volume of urine is reached. However, this method does not allow for precise control of the volume of urine in the bladder.

Thus, it may be beneficial to provide an exemplary catheter which can control the volume of urine in the bladder, and that can overcome at least some of the deficiencies described herein above.

SUMMARY OF EXEMPLARY EMBODIMENTS

An exemplary catheter can be provided which can include, for example, a first inflation arrangement configured, in operation, to substantially seal and/or lock a catheter in the bladder when inflated, a second inflation arrangement configured, in operation, to substantially float in or on urine when inflated, where the second arrangement can be located at a predetermined distance from the first inflation arrangement. An aperture can be provided between the first inflation arrangement and the second inflation arrangement, where the first and second arrangements can cause the aperture to be (i) open when the second inflation arrangement can be located at a first position relative to the first inflation arrangement, and (ii) closed when the second inflation arrangement can be located at a second position relative to the first inflation arrangement, and where the second position can be different than the first position.

The first inflation arrangement and the second inflation arrangements can include balloons. The first inflation arrangement can include a liquid having a density substantially equal to or greater than the density of water, and the second inflation arrangement can include a liquid or gas having a density that can be less than the density of water, which can include oil, or air. At the first position, the second inflation arrangement can be positioned in a substantially parallel manner to the first inflation arrangement, and, at the second position, the second inflation arrangement can be positioned in a non-parallel manner to the first inflation arrangement. At the first position, the second inflation arrangement can be located at a first location relative to the first inflation arrangement, and, at the second position the second inflation arrangement can be located at a second location relative to the first inflation arrangement, the second location being different than the first location. The first location can be further away from the first inflation arrangement than the second location.

In some exemplary embodiments of the present disclosure, a hinge(s) can be located between the first inflation arrangement and the second inflation arrangement, which can be located substantially near the aperture. A spring(s) can be located between the first inflation arrangement and the second inflation arrangement. The first inflation arrangement can be further configured to anchor the catheter to the bladder. A mechanism can be configured to cause the aperture to remain open in the first position and the second position. A heating arrangement, which can be a radio frequency heating arrangement, can be configured to apply heat to the bladder.

A further exemplary embodiment can include a catheter, which can include, for example, an inflation arrangement configured to substantially seal a bladder when inflated, an aperture provided at a first distance from the inflation arrangement, and a junction connected to the inflation arrangement provided at a second distance from the inflation arrangement. A first portion can be connected to the junction. A first valve can be configured to selectively facilitate a flow of liquid through the first portion, and a second portion can be connected to the junction. A second valve can be configured to selectively facilitate the flow of the liquid through the second portion. The first valve can be a ball valve, and the second valve can be a check valve, which can include a spring. The second valve can be configured to facilitate the flow of liquid when the spring is compressed. The inflation arrangement can be further configured to anchor the catheter to the bladder. The junction can be a T-junction and/or a Y-junction. A heating arrangement, which can be a radio frequency heating arrangement, can be configured to apply heat to the bladder.

These and other objects, features and advantages of the exemplary embodiments of the present disclosure will become apparent upon reading the following detailed description of the exemplary embodiments of the present disclosure, when taken in conjunction with the appended claims.

BRIEF DESCRIPTION OF THE DRAWINGS

Further objects, features and advantages of the present disclosure will become apparent from the following detailed description taken in conjunction with the accompanying Figures showing illustrative embodiments of the present disclosure, in which:

FIGS. 1A and 1B are side views of the exemplary catheter according to an exemplary embodiment of the present disclosure, in a relatively empty bladder and a relatively full bladder, respectively;

FIGS. 2A-2C are further side views of the exemplary catheter of FIGS. 1A and 1B according to the exemplary embodiment of the present disclosure;

FIGS. 3A and 3B are even further views of the exemplary catheter of FIGS. 1A and 1B according to the exemplary embodiment of the present disclosure;

FIGS. 5A-5I are side views of the exemplary catheter according to a further exemplary embodiment of the present disclosure;

FIGS. 7A and 7B are side views of an even further exemplary embodiment of the exemplary catheter according to another exemplary embodiment of the present disclosure.

Figure 4B:
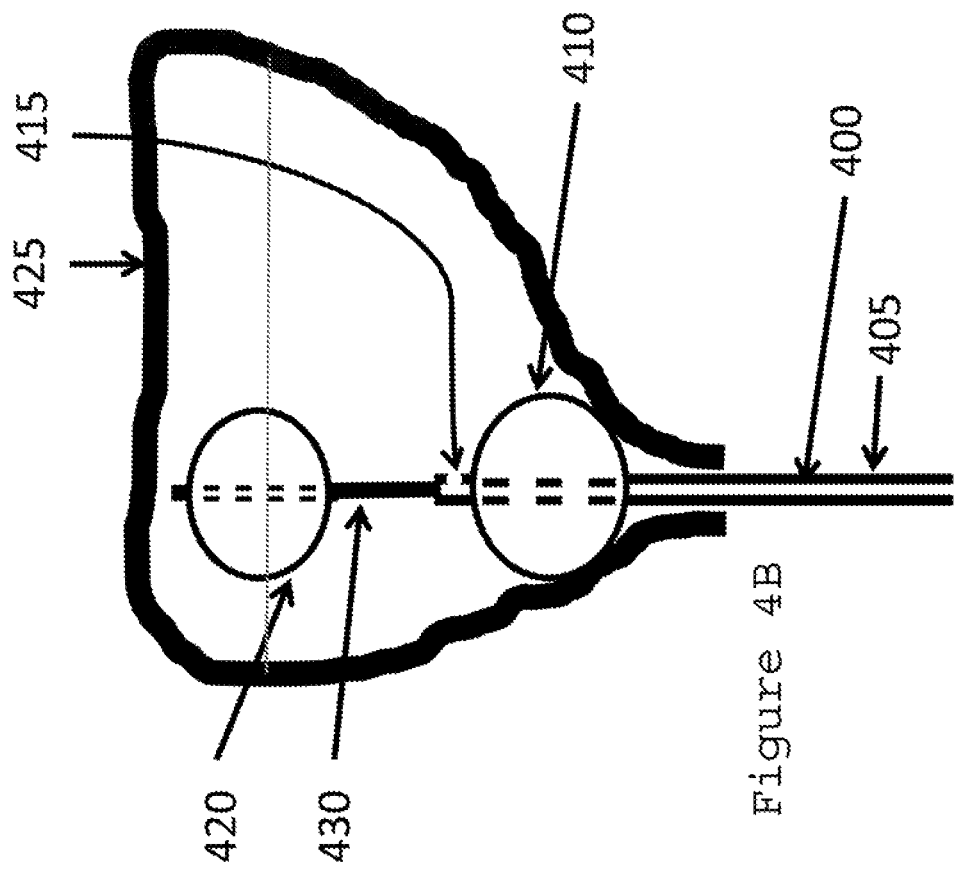
FIGS. 4A and 4B are still further views of the exemplary catheter of FIGS. 1A and 1B according to an exemplary embodiment of the present disclosure.

Throughout the drawings, the same reference numerals and characters, unless otherwise stated, are used to denote like features, elements, components or portions of the illustrated embodiments. Moreover, while the present disclosure will now be described in detail with reference to the figures, it is done so in connection with the illustrative embodiments and is not limited by the particular embodiments illustrated in the figures and the appended claims.

DETAILED DESCRIPTION OF EXEMPLARY EMBODIMENTS

The exemplary apparatus, according to various exemplary embodiments of the present disclosure, described herein includes a urinary catheter with valve that can open once urine accumulates in the urinary bladder to a specific level. The exemplary catheter can include an indwelling urinary catheter with two, or more, balloons. The balloons can be inflated after catheter insertion, for example, when both are already resident in the urinary bladder. The first balloon can function as an anchor to the catheter inside the urinary bladder, and can be filled with a substance (e.g., a liquid, solid and/or gas) with a density equivalent to the density of water or higher. The second balloon can function as a float, and can be inflated with a substance having a density less than that of water (e.g., oil and/or air). The float (e.g., second) balloon can float on or in urine, and once the bladder fills with urine to a specific volume a valve can open, facilitating the drainage of urine. Once the urine volume decreases below a specific preset volume, the valve can close. This exemplary configuration can facilitate the bladder urine volume to remain within a specified tight range, ensuring or facilitating a continuous filling of the bladder, while hindering the bladder from overfilling. This can ensure or facilitate the urinary bladder to stay full, while keeping the patient safe from renal failure due to a bladder obstruction.

For example, FIG. 1A illustrates the exemplary catheter 100 in a closed position (e.g., with a substantially empty bladder), and FIG. 1B illustrates the exemplary catheter in the opened position (e.g., with a full or substantially full bladder). A urine drainage tube 105 can drain the urinary bladder through the urethra. An anchoring balloon 110 (e.g., provided for anchoring the catheter 100 in the urinary bladder) can be inflated once the catheter is in the urinary bladder. The anchoring balloon 110 can be filled with a liquid having a density that can be equal to or higher than the density of urine (e.g., water). The part of the drainage tube inside the urinary bladder can be sealed all over except for a drainage hole 115 for draining urine from the urinary bladder 135 through the urine drainage tube 105. The drainage hole 115 can be closed when the valve hinge 120 is in the bent position, and can open once it is in the upright position. An arm 125 can connect the valve hinge 120 to a floating balloon 130.

The floating balloon 130 can be filled with a substance having a density lower than that of urine or water (e.g., oil and/or air), after the insertion of the catheter 100 into the urinary bladder 135. The catheter can have multiple lumens (e.g., 3). A first lumen can be the urine drainage tube 105, a second lumen can be for inflation and deflation of the anchor balloon 110, and a third lumen can be provided for inflation and deflation of the floating balloon 130. The bladder volume control mechanism can be used continuously in its active form as shown in FIGS. 1A and 1B, and can be used together with the activation and deactivation mechanisms shown in FIGS. 2A-2C. An umbrella like activation knob 240 can be attached to stabilizing strips 245. Once the activation knob 240 is provided in its "On" position, the stabilizing strips 245 can be placed in a loose mode, facilitating the floating balloon 130 and the arm 125 connecting the floating balloon 130 to the valve hinge 120 to be movable. This configuration can facilitate the drainage hole 115 to be opened once the bladder is full, (see, e.g., FIG. 2B), and to be closed when the bladder is less than full. (See, e.g., FIG. 2C). When the activation knob 240 is provided in the "Off" mode (see, e.g., FIG. 2A), the stabilizing strips 245 can be provided in a "tense mode," thus, keeping or maintaining the drainage hole 115 in an open position, regardless of the bladder's fill status. This can result in a continuous full drainage of the bladder.

FIGS. 3A and 3B illustrate a further exemplary catheter 300, according to another exemplary embodiment of the present disclosure. For example, FIG. 3A shows the exemplary catheter 300 in a closed position (e.g., with an empty bladder) and FIG. 3B illustrates the exemplary catheter 300 in an open position (e.g., with a full bladder).

As shown in FIGS. 3A and 3B, a urine drainage tube 305 can drain the urinary bladder 325 through the urethra. Urine drainage tube 305 can be inserted into a sleeve 330. An anchoring balloon 310 (e.g., provided for anchoring the catheter 300 in the urinary bladder 325) can be inflated when the catheter 300 is in the urinary bladder 325, and can stabilize the catheter 300 in the urinary bladder 325. The anchoring balloon 310 can be filled with a substance having a density equal to or higher than the density of urine (e.g., water). The urine drainage tube 305 can be connected to the floating balloon 320 at its urinary bladder end, and can slide in and out of the sleeve 330. When the bladder is empty, the urine drainage tube 305 can slide fully into the sleeve 330, can close the urine drainage hole 315, and can prevent the drainage of urine, as shown in FIG. 3A.

When the bladder is full, as shown in FIG. 3B, the urine drainage tube 305 can slide out of the sleeve 330 to a specific or predetermined extent or level that can expose the urine drainage hole 315, and can facilitate the drainage of urine. The floating balloon 320 can be filled with a material having a density lower than that of urine or water, (e.g., oil and/or air). The catheter can have multiple lumens (e.g., 4), with a first lumen can be the urine drainage tube 305, a second lumen can be the sleeve 330, a third lumen can be provided for inflation and deflation of the anchor balloon 310, and a fourth lumen can be provided for inflation and deflation of a floating balloon 320. A bladder volume control mechanism can be used continuously in its active form, and/or can be used together with an exemplary activation and deactivation mechanism. When the activation mechanism is in the "On" position, the positions of the urine drainage tube 305 and urine drainage hole 315 can be controlled by the floating balloon 320 as described above. When the activation mechanism is in the "Off" mode, a stabilizing mechanism can maintain the urine drainage tube 305 in its maximal slide-out position in the sleeve 330, thus keeping the urine drainage hole 315 open regardless of the amount of urine in the bladder, resulting in a continuous full drainage of the bladder.

Figure 4A:
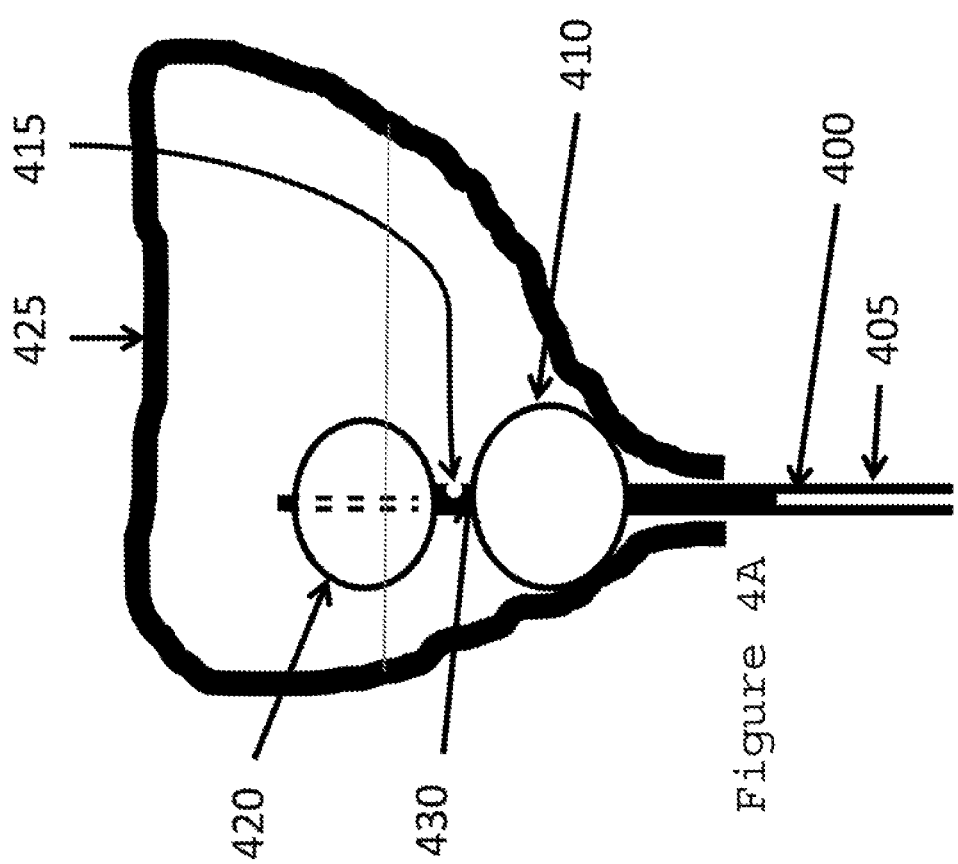

FIGS. 4A and 4B illustrate a further exemplary catheter 400 according to a further exemplary embodiment of the present disclosure. For example, the exemplary catheter 400 is illustrated in FIG. 4A in the closed position (e.g., with an empty bladder), and illustrated in FIG. 4B in the opened position (e.g., with a full bladder).

As shown in FIGS. 4A and 4B, a urine drainage tube 405 of the catheter 400 can drain the urinary bladder 425 through the urethra. An anchoring balloon 410 (e.g., provided for anchoring the catheter in the urinary bladder 425) can be inflated once the catheter can be in the urinary bladder 425. The anchoring balloon 410 can be filled with a substance having a density equal or higher to the density of urine (e.g., water). A sliding arm 430 can connect to a floating balloon 420 from one end, and can slide in and out of the urine drainage tube from the other end. When the sliding arm 430 slides into the urine drainage tube 405, it can close the urine drainage hole 415, and prevent drainage of urine, as shown in FIG. 4A. When the sliding arm 430 slides out of the urine drainage tube 405, the urine drainage hole 415 can open, and can facilitate the drainage of urine. The floating balloon 420 can be filled with a substance having a density lower than that of urine or water (e.g., oil and/or air). When the bladder is empty, as shown in FIG. 4A, the sliding arm 430 can slide into the urine drainage tube 405, and can close the urine drainage hole 415. When the bladder fills, as shown in FIG. 4B, the sliding arm 430, driven by the floating balloon 420, can slide out of the urine drainage tube 405, and can open the urine drainage hole 415. An exemplary spring or retraction mechanism can be used to return the sliding arm 430 into the urine drainage tube 405 once the bladder becomes empty.

The exemplary catheter 400 can have multiple lumens (e.g., three), a first lumen can be the urine drainage tube 405, a second lumen can be provided for inflation and deflation of the anchor balloon 410, and a third lumen can be provided for inflation and deflation of the floating balloon 420. The bladder volume control mechanism can be used continuously in its active form, or can be used together with the exemplary activation mechanism and deactivation mechanism. Once the exemplary activation is in its "On" position, the sliding arm 430 position can be controlled by the floating balloon 420 location as described above. When the exemplary activation mechanism is in the "Off" mode, a stabilizing mechanism can maintain the sliding arm 430 in its maximal position out of the urine drainage tube, keeping the drainage hole 415 open regardless of the bladder volume, which can result in continuous full drainage of the bladder.

Figure 5B:
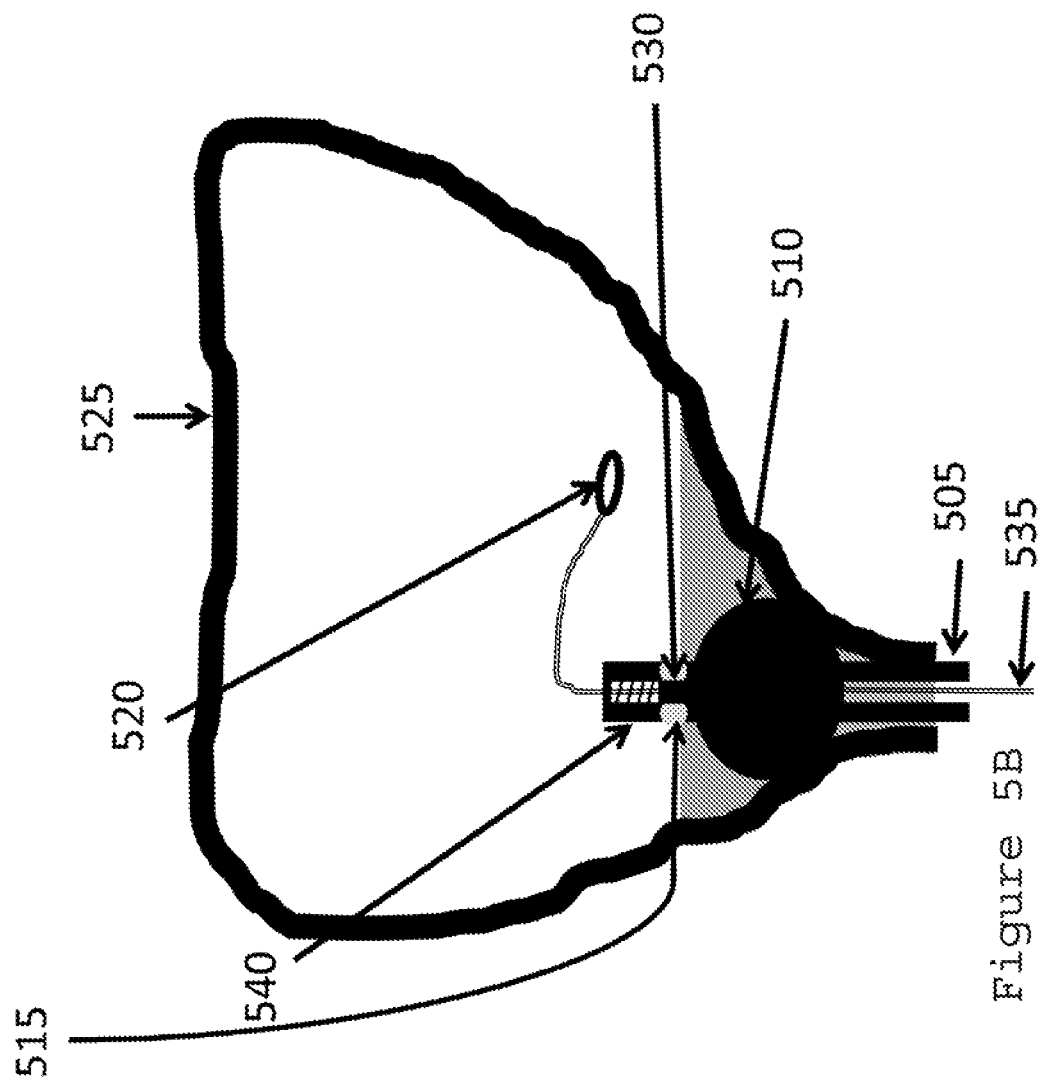
Figure 5E:
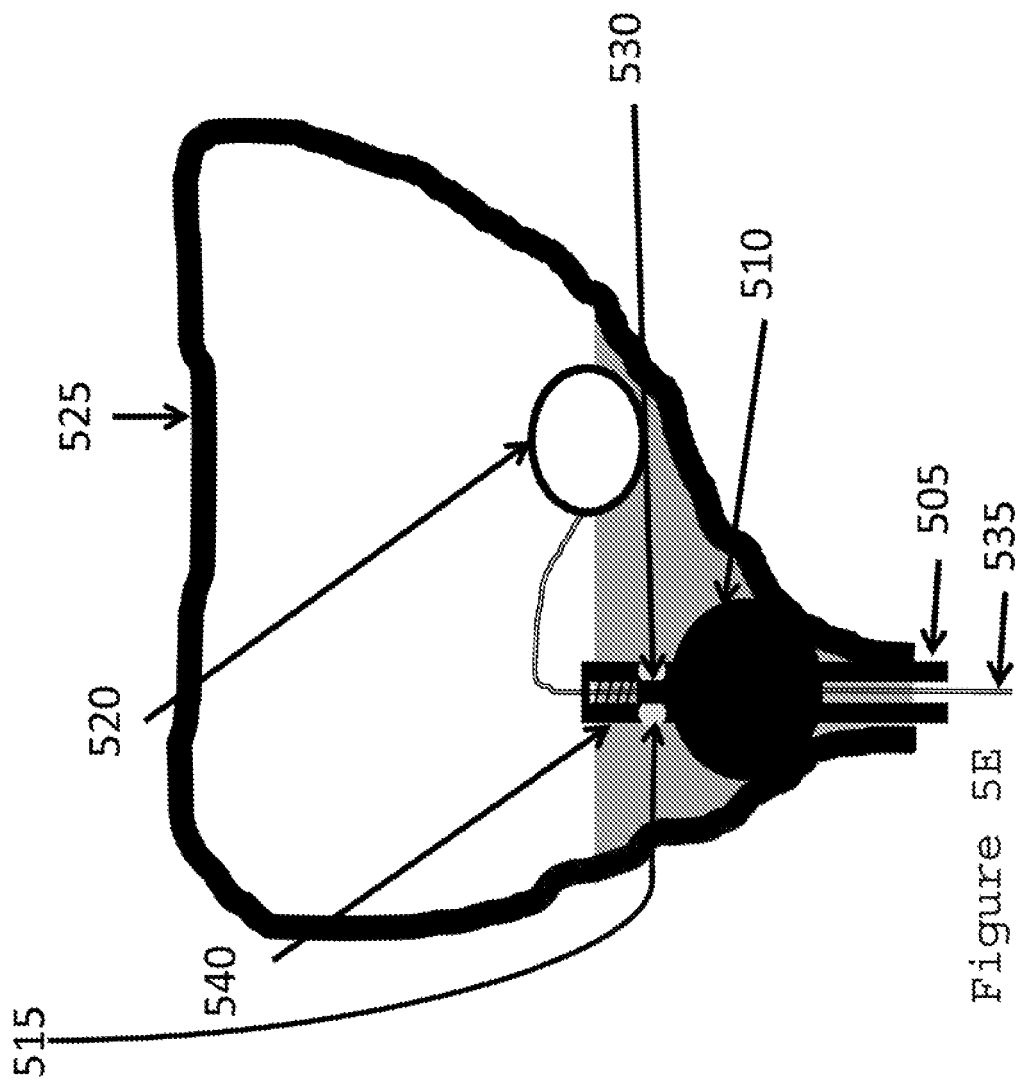
Figure 5F:
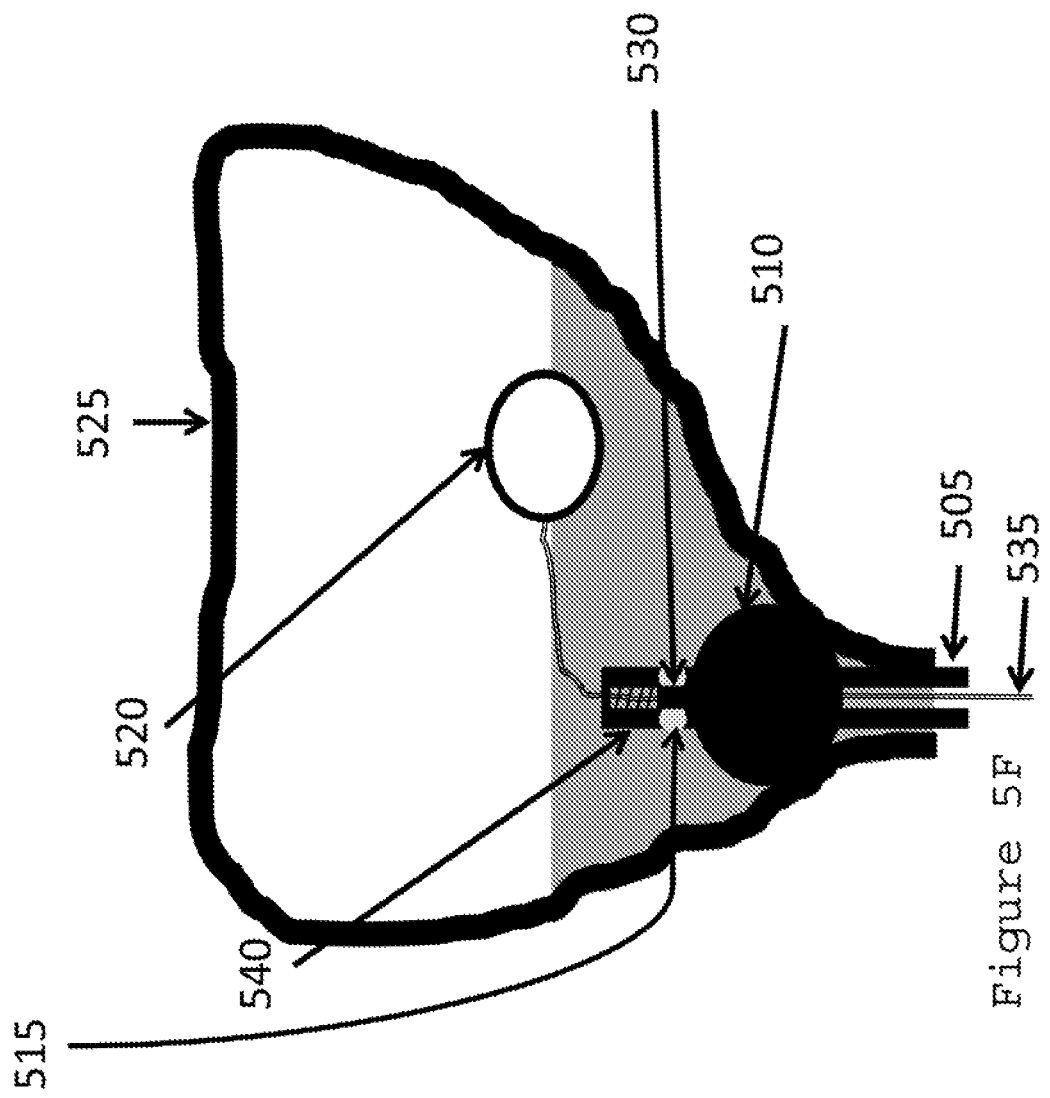
Figure 5G:
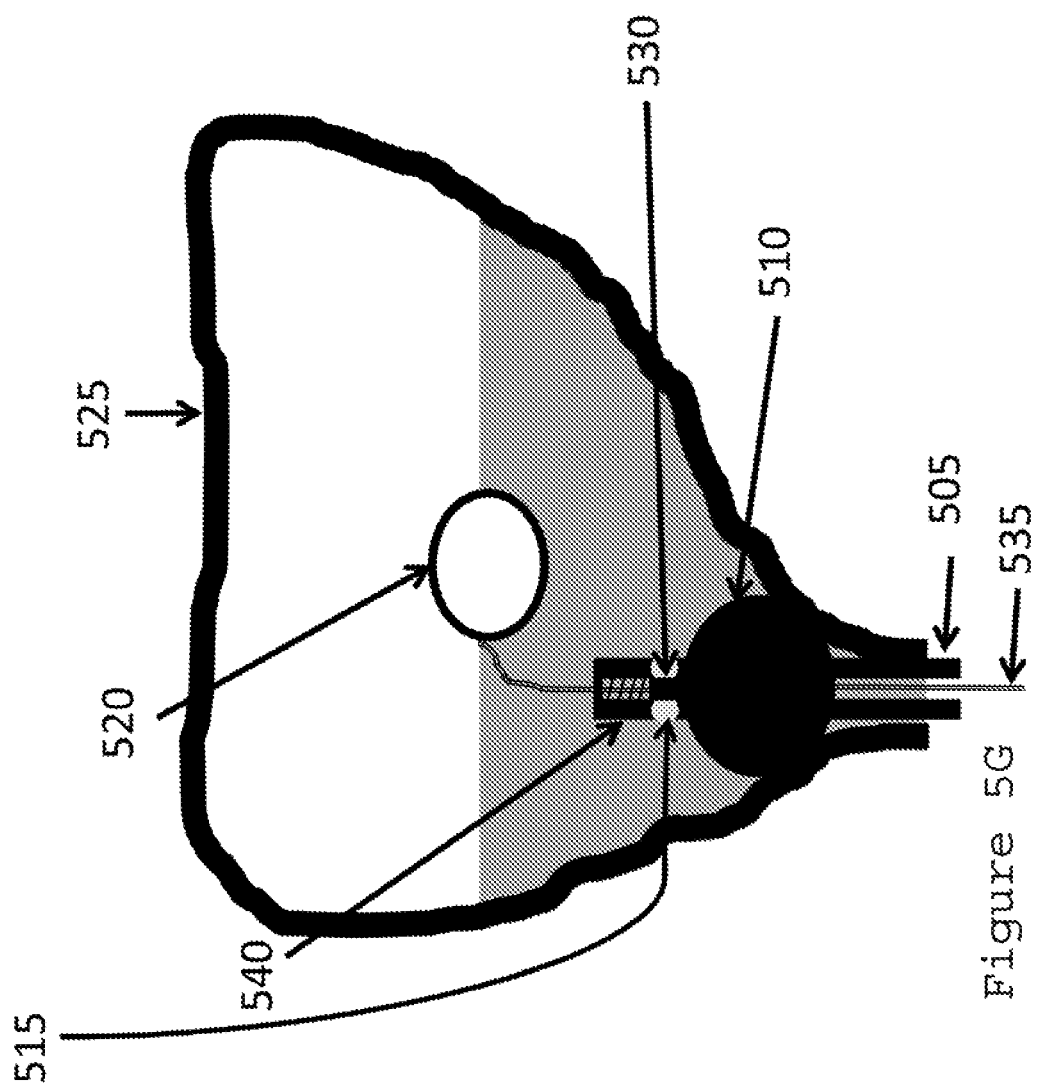
Figure 5H:
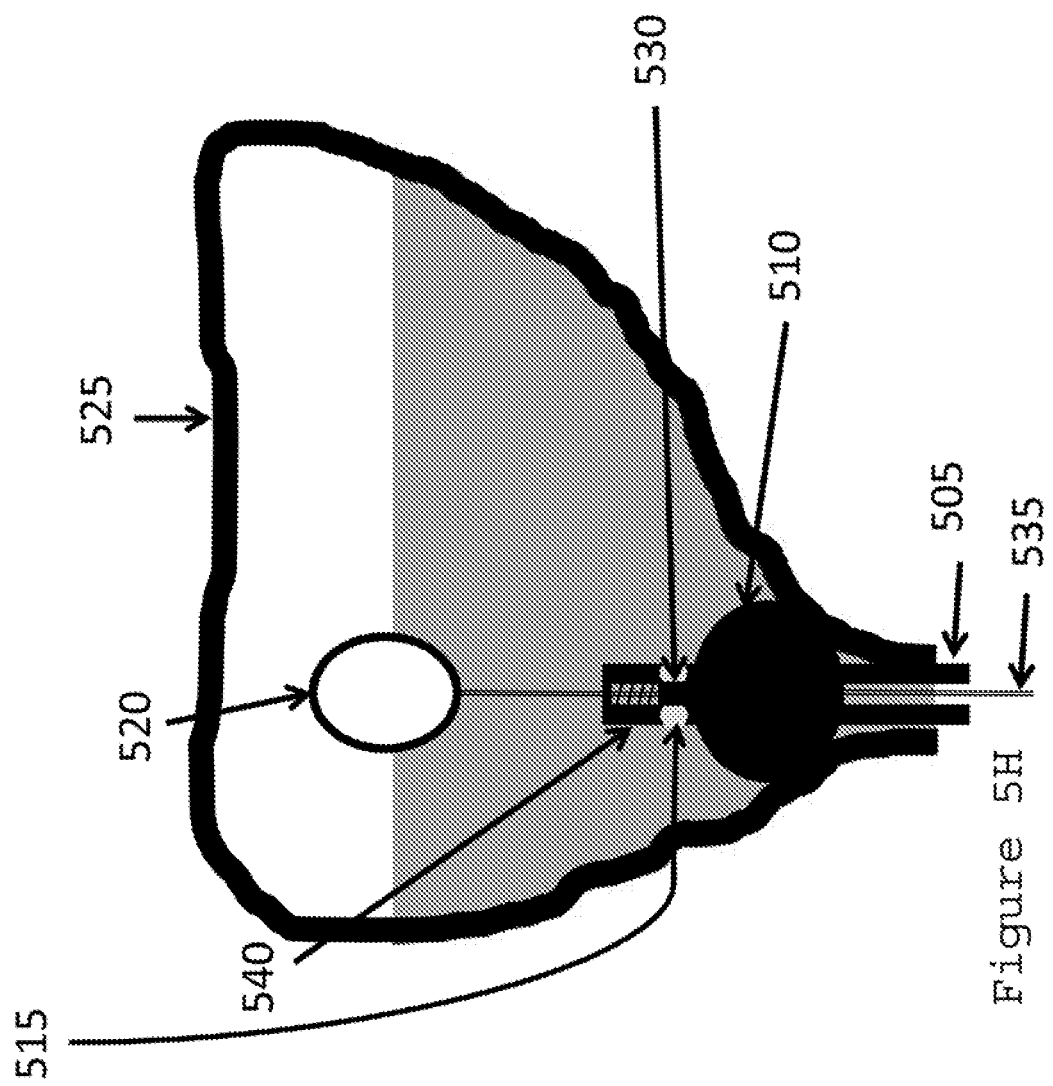
Figure 5I:
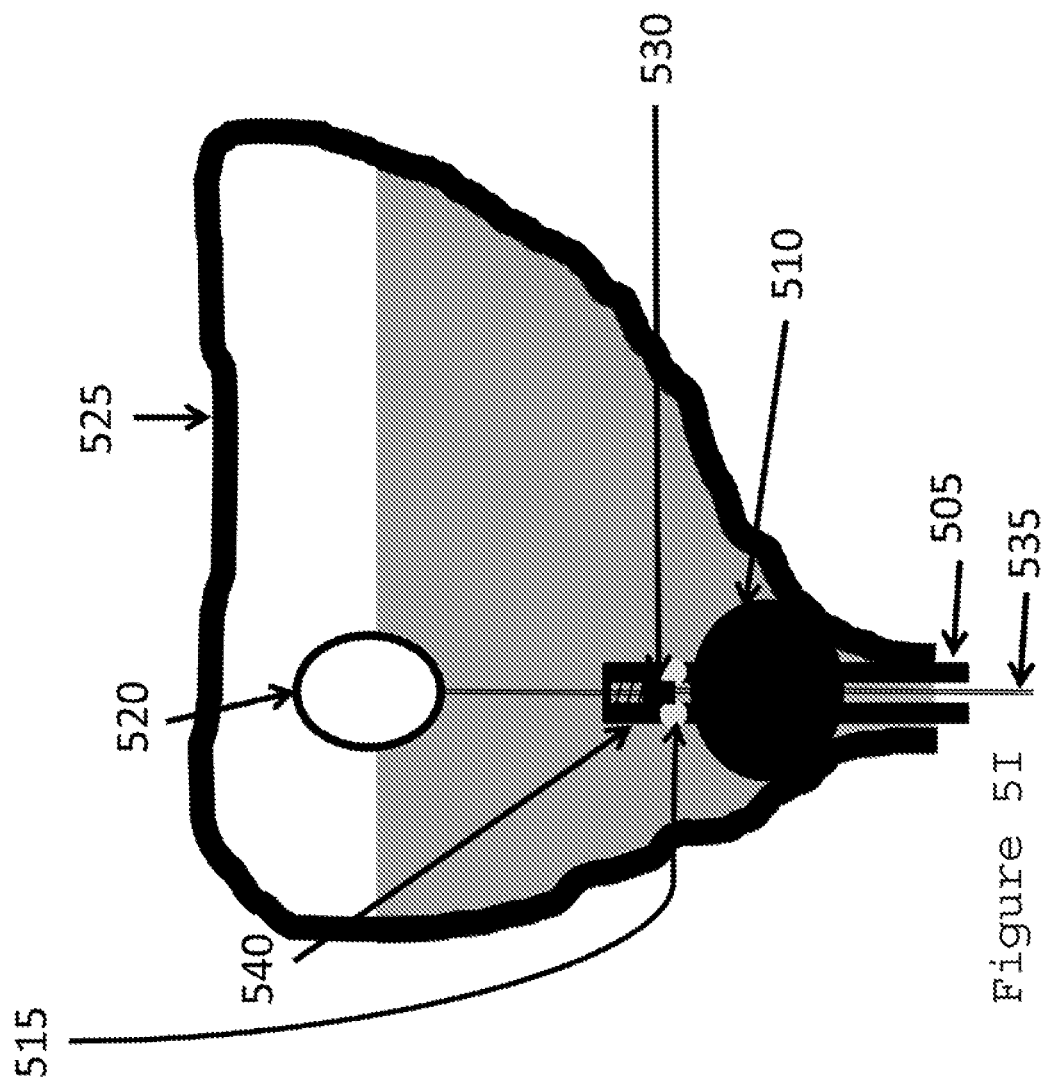

FIGS. 5A-5I illustrate the exemplary catheter 500 for control of bladder urine volume in various configurations and/or states, according to yet another exemplary embodiment of the present disclosure. For example, FIGS. 5A-5C illustrate the exemplary catheter 500 with an almost empty urinary bladder, FIGS. 5D-5H illustrate the exemplary catheter in a partially full bladder, and FIG. 5I illustrates the exemplary catheter in a full bladder. A urine drainage tube 505 can drain the urinary bladder 525 through the urethra. An anchoring balloon 510 (e.g., for anchoring the catheter in the urinary bladder) can be inflated once the catheter 500 is in the urinary bladder. The anchoring balloon 510 can be filled with a substance having a density equal to or higher than the density of urine (e.g., water). A cylinder-shaped plug 530 can connect to the tube 535 to inflate a floating balloon 520. The tube 535 can connect to the floating balloon 520, and the floating balloon 520 can be filled with a substance having a density that is lower than the density of urine or water (e.g., oil and/or air).

When the bladder is almost empty, as shown in FIG. 5A-5C, or only partially full, as shown in FIGS. 5D-5H, the tube 535 does not open the cylinder-shaped plug 530, the spring 540 stays in its uncompressed state, and the drainage aperture 515 remains closed. When the bladder is full or filled to a specified amount, as shown in FIG. 5I, the floating balloon 520 floats in the urine, and stretches the tube 535, which draws the cylinder shaped plug 530, and compresses the spring 540. This can result in the opening of the drainage aperture 515, thus facilitating the flow of urine from the urinary bladder 525 to the urine drainage tube 505. When urine in the bladder reaches a level below a specified or predetermined amount, the spring 540 can return to the uncompressed state, and the cylinder-shaped plug 530 closes the drainage aperture 515.

The exemplary catheter 500 can have multiple lumens (e.g., three). For example, a first lumen can be urine drainage tube 505, a second lumen can be for inflation and deflation of the anchor balloon 510, and a third lumen can be tube 535 for inflation and deflation of the floating balloon 520. An exemplary bladder volume control mechanism can be used continuously in its active form as shown in FIGS. 5A-5I, and/or can be used together with activation and deactivation mechanism, as shown in FIGS. 6A and 6B.

Figures 6A, 6B:
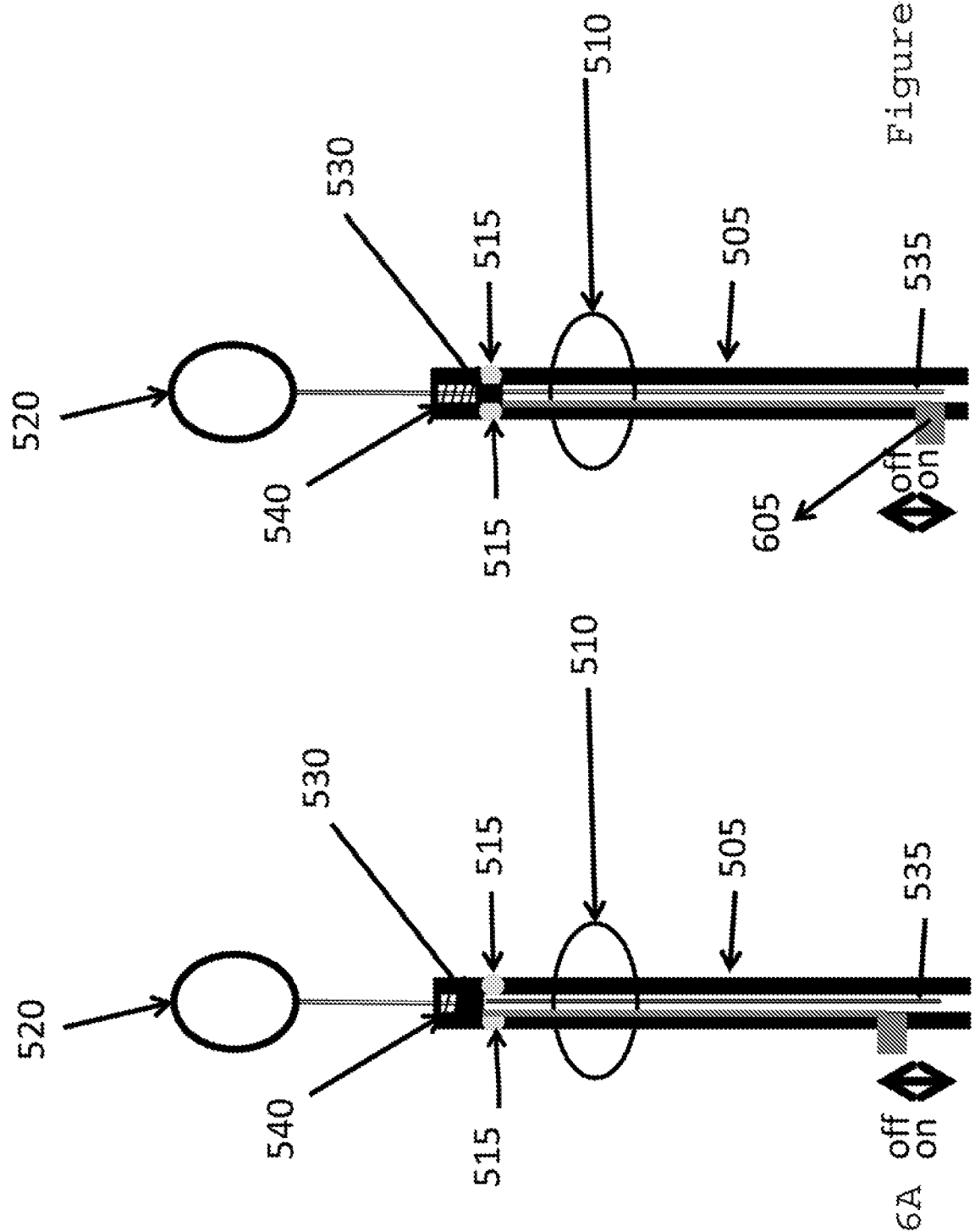
FIGS. 6A and 6B are further views of the exemplary catheter of FIGS. 5A-5I according to a further exemplary embodiment of the present disclosure.

An exemplary deactivation mechanism can include a spring 540 that can be continuously compressed regardless of the float balloon condition, which can result in a continuous opening of the drainage aperture 515, as shown in FIG. 6A. This can occur when the activation knob 605 is in its "Off" position. (See, e.g., FIG. 6A). When the activation knob 605 is in its "On" position, the deactivated knob can release the spring 540, as shown in FIG. 6B, and can keep the spring 540 under the control of the float balloon 520 and the tube 535. Such exemplary operation/configuration can be used to open the drainage aperture 515, once the balloon 520 sufficiently floats, by raising the cylinder-shaped plug 530 and by compressing the spring 540. The specified amount of urine in the bladder can be chosen by selecting the length of the part of the tube 535 between the cylinder-shaped plug 530 and the floating balloon 520. This exemplary length can define the exemplary catheters in addition to using the French diameter that can be tailored to the urethral diameter. Selecting the exemplary length can depend on the expected urine capacity, and the distance between the bladder neck and the dome of the bladder once the bladder is full with urine.

FIGS. 7A and 7B illustrate another exemplary catheter 700 according to a still further exemplary embodiment of the present disclosure. For example, the exemplary catheter 700 illustrated in FIG. 7A is in a closed position (e.g., with an empty bladder), and illustrated in FIG. 7B in an opened position (e.g., with a full bladder).

A urine drainage tube 705 of the exemplary catheter 700 can drain the urinary bladder 720 through the urethra. An anchoring balloon 710 (e.g., for anchoring the catheter in the urinary bladder 720) can be inflated once the catheter can be in the urinary bladder 720. The part of the urine drainage tube 705 inside the urinary bladder 720 can be fully or mostly sealed except for a drainage hole 715 for draining urine from the urinary bladder 720 through the urine drainage tube 705. The drainage hole 715 can be continuously open. The urine drainage tube 705, once outside the body, can split into two tubes.

The first tube can be connected to a check valve 725, such as ball and/or a spring valve, that can automatically open when the urine pressure exceeds a specific preset limit, (see, e.g., FIG. 7B), and can close if the urine pressure can be less than a preset limit. (See, e.g., FIG. 7A).

The exemplary catheters described herein above can be used to treat patients with intra-vesical medications such as Bacillus Calmette-Guerin ("BCG"), chemotherapy such as Mitomycin C, Cisplatin, pegelated drugs and/or antibiotics. The concentration and the temperature of the medication inside the bladder can be maintained within a specified target range by continuously filling and draining the bladder with the target material. Additionally, or alternatively, the concentration and the temperature of the medication inside the bladder can be kept within a specified target range by adding concentrated medication per each volume of urine drained so that the concentration of the medication in the bladder is kept constant and/or by combining the bladder filling mechanism with various suitable heating arrangements such as a radio frequency ("RF") heating arrangement. (See, e.g., RF heating arrangement 140 from FIG. 1A and RF heating arrangement 745 from FIG. 7A). This can result in exposure of the bladder to the medication while draining the bladder only as necessary.

The second tube can be controlled by a ball and socket valve 730, and can be opened and/or closed manually, for example, when in an open position, it can facilitate the urine to flow in the second tube regardless of the urine pressure. When the ball and socket 730 valve is in the closed position, urine cannot drain in the second tube, and urine drains only in the first (e.g., parallel) tube through the ball and spring check valve 725 when the pressure exceeds specific limit. This can result in the filling of the urinary bladder 720 as long as the specific pressure is not exceeded. Urine from either of the tubes can drain into the urine drainage tube connecting the catheter to the urine collecting bag 740. The exemplary urinary pressure check valve 725, can be or can include a ball and spring valve, and/or any check pressure valves used for ventriculo-peritoneal shunts, with the only difference being that the exemplary urinary valve can be adapted to the desired the urinary bladder pressures. In addition or alternatively, check valves, such as gravitational shunt valves, can be used to facilitate modified bladder drainage according to the patient position, and to facilitate tuning of the opening pressure to clinical needs and desired bladder filling. Unlike ventriculo-peritoneal shunts, the exemplary catheters described herein can contain a parallel channel with a ball and socket valve 730 that can actual shunt the check valve when bladder filling is not needed.

The exemplary urinary catheter, according to various exemplary embodiments of the present disclosure, can be used to control the urinary bladder urine volume, and can include a urine drainage tube, a valve mechanism that can open and close the urine drainage tube, an anchoring balloon filled with water, which can be inflated after inserting the catheter into the bladder in order to keep the catheter in place, and a second float balloon, filled with a substance having a density less than water (e.g., oil and/or air), and can be inflated after insertion of the catheter into the bladder. The float balloon can control the valve mechanism, and can open it when the bladder is full to a preset amount, and can close it when the bladder fullness is less than the preset amount.

The exemplary urinary catheter can be inserted through the urethra into the urinary bladder, with the valve which, when open, can facilitate the drainage of urine from the bladder, and when closed, can prevent drainage of urine from the bladder. The valve can be open only when the bladder is full to a specific amount, and can be closed when the volume of urine in the bladder can be less than specific amount. The valve can be controlled by an exemplary mechanical system that can include a hinge, and a balloon at the edge of the hinge that when inflated with air or oil, can function as a float. The valve can open when the balloon is fully afloat in the urine in the bladder, and can be closed when the float is not fully floating in the urine. The weight and/or position of the float balloon can be modulated so that the valve can open with a changing amount of urine (e.g., according to clinical needs).

The valve mechanism can be deactivated by a stabilizing mechanism, such that the valve can be kept open when the patients is out of the hospital, and the valve mechanism can be reactivated before a procedure that needs the bladder to be full (e.g., about 1-2 hours).

The exemplary urinary catheter can control urinary bladder volume. The exemplary catheter can have a urine drainage tube, an anchoring balloon filled with water which can be inflated after inserting the catheter into the bladder in order to keep the catheter in place. The portion of the drainage tube outside the body can be split into two tubes. The first tube can be connected to a check valve (e.g., a ball or a spring valve), that can automatically open when the urine pressure exceeds a specific preset limit, and can close if urine pressure is less than the specific limit. A second tube can be controlled by a ball and socket valve where the ball and socket valve can be opened and closed manually, and when in the open position, can facilitate urine to flow in the second tube regardless of the urine pressure. When the ball and socket valve is in a closed position, urine may not drain in the second tube, and urine may drain only in the first tube when the pressure exceeds the specific limit, resulting in filling of the urinary bladder as long as the specific pressure is not exceeded.

Each of the exemplary valves can be or include a gravitational valve that can facilitate modified bladder drainage according to the patient position. The valve can be at the catheter outlet, outside the body of the patient, and before the connection to the urine collection bag. The exemplary valve mechanism can be shunted by a parallel draining tube, where the shunting mechanism can be tuned to the open position when the bladder filling is not needed, and can be tuned to closed position when the bladder filling mechanism is needed, facilitating the urine to flow through the check valve once the pre-specified urine pressure can be achieved.

While the exemplary catheter has been described above for us with radiation oncology to fill the bladder, the exemplary catheter can also be used to treat patients with intra-vesical chemotherapy or medications. This can result in exposure of the bladder to the medication, while draining the bladder only as necessary The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements, and procedures which, although not explicitly shown or described herein, embody the principles of the disclosure and can be thus within the spirit and scope of the disclosure. Various different exemplary embodiments can be used together with one another, as well as interchangeably therewith, as should be understood by those having ordinary skill in the art. In addition, certain terms used in the present disclosure, including the specification, drawings and claims thereof, can be used synonymously in certain instances, including, but not limited to, for example, data and information. It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein above, it is explicitly incorporated herein in its entirety. All publications referenced are incorporated herein by reference in their entireties.

What is claimed is:

1. A catheter comprising:
   a first inflation arrangement configured, in operation, to substantially seal a bladder when inflated;
   a second inflation arrangement configured, in operation, to substantially float in urine when inflated, wherein the second arrangement is located at a predetermined distance from the first inflation arrangement; and
   an aperture provided between the first inflation arrangement and the second inflation arrangement, wherein at least one of the first and second arrangements cause the aperture to be (i) open when the second inflation arrangement is located at a first position relative to the first inflation arrangement, and (ii) closed when the second inflation arrangement is located at a second position relative to the first inflation arrangement, and wherein the second position is different than the first position.

2. The catheter of claim 1, wherein the first inflation arrangement and the second inflation arrangements include balloons.

3. The catheter of claim 1, wherein the first inflation arrangement includes a substance having a density substantially equal to or greater than a farther density of water.

4. The catheter of claim 1, wherein the second inflation arrangement includes a substance having a density that is less than a further density of water.

5. The catheter of claim 4, wherein the substance provided in the second inflation arrangement includes at least one of oil, air or gas.

6. The catheter of claim 1, wherein, at the first position, the second inflation arrangement is positioned in a substantially parallel manner to the first inflation arrangement, and wherein, at the second position, the second inflation arrangement is positioned in a non-parallel manner to the first inflation arrangement.

7. The catheter of claim 1, wherein at the first position, the second inflation arrangement is located at a first location relative to the first inflation arrangement, and wherein at the second position the second inflation arrangement is located at a second location relative to the first inflation arrangement, the second location being different than the first location.

8. The catheter of claim 7, wherein the first location is further away from the first inflation arrangement than the second location.

9. The catheter of claim 1, further comprising at least one hinge located between the first inflation arrangement and the second inflation arrangement.

10. The catheter of claim 9, wherein the at least one hinge is located substantially near the aperture.

11. The catheter of claim 1, further comprising at least one spring located between the first inflation arrangement and the second inflation arrangement.

12. The catheter of claim 1, wherein the first inflation arrangement is further configured to anchor the catheter to the bladder.

13. The catheter of claim 1, further comprising a mechanism configured to cause the aperture to remain open in the first position and the second position.

14. The catheter of claim 1, further comprising a heating arrangement configured to apply heat to the bladder.

15. The catheter of claim 14, wherein the heating arrangement includes a radio frequency heating arrangement.

* * * * *